May 23, 1972

H. B. WILFONG

Plant Pat. 3,190

CHRYSANTHEMUM PLANT

Filed Sept. 23, 1970

2 Sheets-Sheet 1

United States Patent Office

Plant Pat. 3,190
Patented May 23, 1972

3,190

CHRYSANTHEMUM PLANT

Harry B. Wilfong, Newton, N.C., assignor to Yoder Brothers, Inc., Barberton, Ohio

Filed Sept. 23, 1970, Ser. No. 74,942
Int. Cl. A01h *5/00*
U.S. Cl. Plt.—77 1 Claim

The present invention comprises a new and distinct variety of chrysanthemum plant which is a sport of the variety known in the United States as White Pink Chief, an unpatented but commercial variety of Yoder Brothers, Inc., Barberton, Ohio.

The new variety is similar in many respects to White Pink Chief, having the same characteristics of:

(1) Flower color.

(2) Flower form.

(3) Foliage color.

(4) Early cloth removal adaptability.

The new variety is distinguished from White Pink Chief by the following characteristics:

(1) Flower one inch larger.

(2) A response of approximately 9 weeks rather than 8 weeks.

(3) Four to six inches more vigor.

(4) Larger foliage.

(5) Stems with a heavier caliper.

The new variety was recognized by me in a greenhouse in Newton, N.C., and was asexually reproduced by cuttings at Barberton, Ohio. The new variety has been found to retain its distinctive characteristics through successive propagations.

My new variety when grown in the vicinity of Barberton, Ohio, has a response period of approximately 9 weeks, and the following detailed description is based on observations made of the new variety in a greenhouse in Barberton, Ohio. The response time and blooming period may vary significantly with varying environmental conditions such as temperature, day length, and light intensity. Suggested flowering in the northern and western United States is from May through October.

Figure 1:
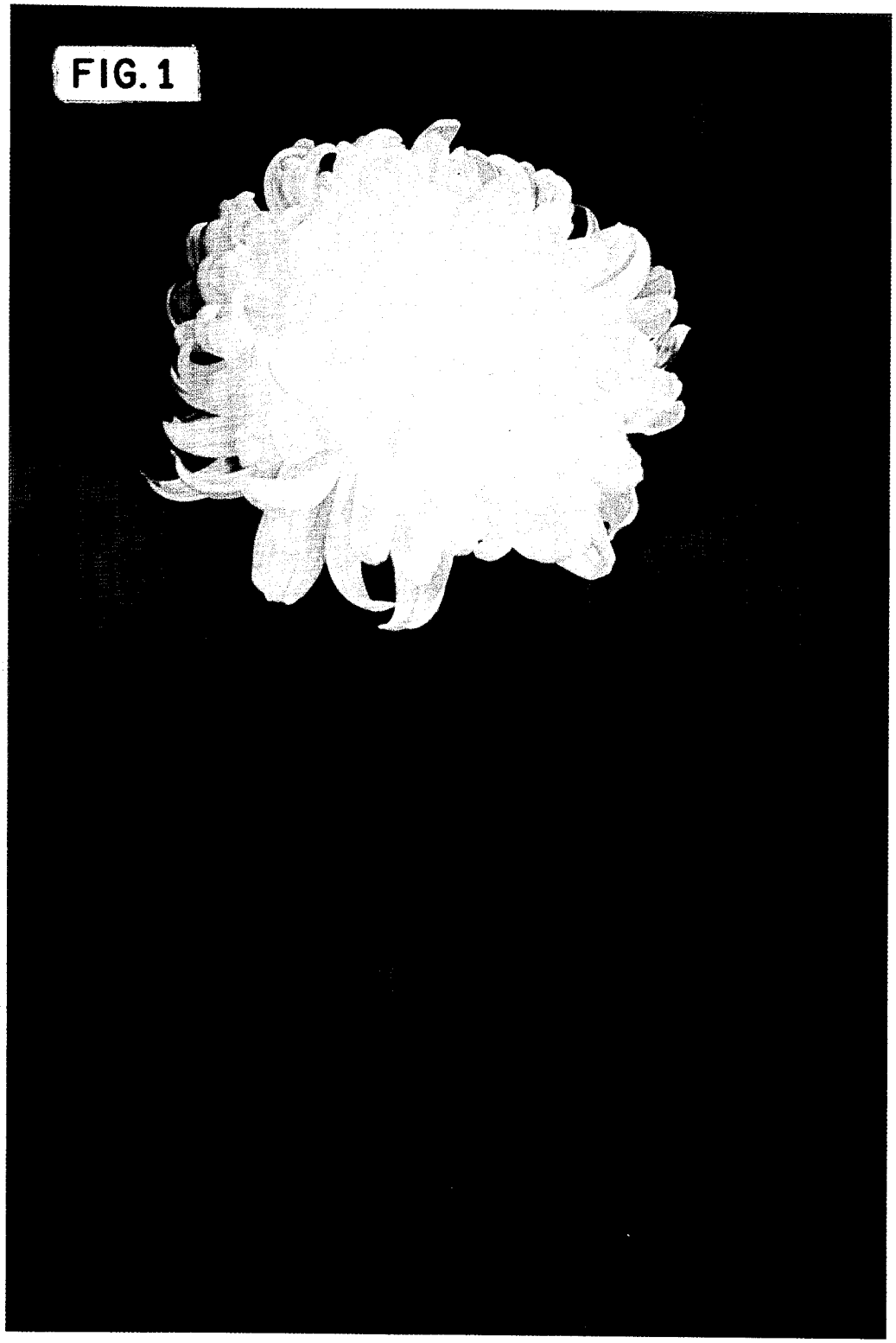
Figure 2:
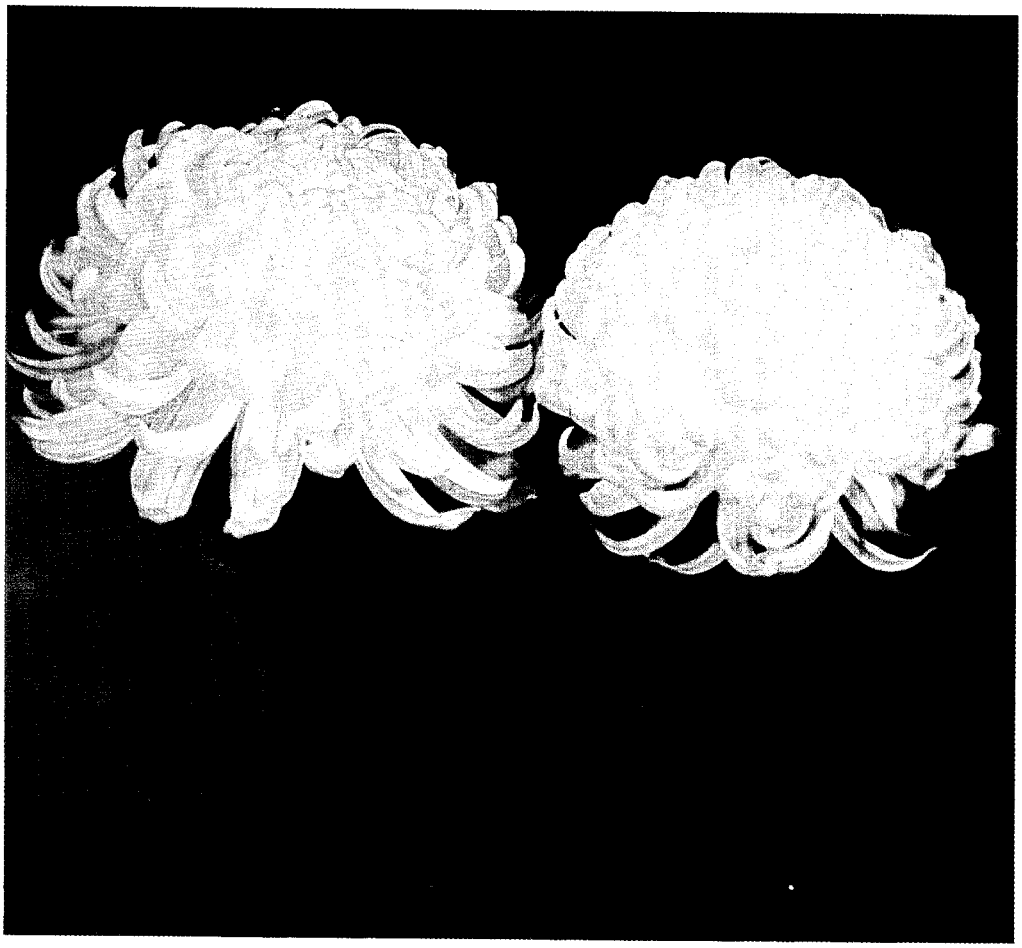

The accompanying drawings show the unique characteristics of my new variety, with the colors being as true as possible with color illustrations of this type. FIG. 1 is of the new variety and FIG. 2 is a comparison of the new variety with the cultivar White Pink Chief, with the new variety appearing on the left in this figure and White Pink Chief on the right.

The following data is based on observations made of the new variety in a greenhouse in Barberton, Ohio. Color references are made to the Munsell Color Book, 1963 edition, and, where meaningful, comparisons made with White Pink Chief.

Botanical classification: *Chrysanthemum morifolium.*

| | Super Chief | White Pink Chief |
|---|---|---|
| Bloom: | | |
| Size | 4½"–5½" | 3½"–4½". |
| Fully expanded | 5"–6" | 4"–5". |
| Borne | Singly on disbudded plant. | Singly on disbudded plant. |
| Stems | Wiry | Wiry. |
| Form | Incurve | Incurve. |
| Permanence | 7–10 days | 7–10 days. |

NOTE.—Color (Munsell)—(for both Super Chief and white Pink Chief):

| | |
|---|---|
| Center of flower, white | 5Y9/1 |
| Base of petals, white | 5Y9/1 |
| Inside of petals, white | N9.5/ |
| Reverse of petals, white | N9.5/ |
| Tonality from a distance-white | N9.5/ |
| Discoloration, white | N9.5/ |

Petals:

*Texture.*—Smooth.

*Appearance.*—Slightly open at base, 2 main keels at bottom; wide at mid-point; tapers evenly to a point.

*Arrangement.*—Composite, whorled on a single receptacle.

*Persistence.*—Resists shatter.

*Fragrance.*—Typical chrysanthemum.

Reproductive organs:

*Stamen, anthers.*—None.

*Pollen.*—None.

*Arrangement.*—Clustered in center of flower, if present.

*Styles.*—Present in both ray and disc florets.

*Length.*—Short.

*Ovaries.*—At base of petals attached to receptacle.

Plant:

*Form.*—Herbaceous.

*Growth.*—Upright.

*Height, depending on culture.*—38"–40" (White Pink Chief—32"–36").

Foliage:

*Top side.*—Green, 7.5GY4/4.

*Size.*—5"–6" long, 2½"–3½" wide (White Pink Chief—4"–5" long, 2¼"–3" wide).

*Quantity.*—Numerous.

*Shape.*—Palmate.

*Texture.*—Coarse.

*Ribs and veins.*—Very prominent.

*Edge.*—Deeply cut.

*Serration.*—Moderate.

*Underside.*—Light green, 7.5GY5/4.

*Stipules.*—Rudimentary.

I claim:

1. A new and distinct variety of chrysanthemum characterized particularly as to improved traits over the parent variety, White Pink Chief, by having 4" to 6" more vigor than parent, one inch larger flowers, larger foliage, heavier caliper stems and one week later response.

No references cited.

ROBERT E. BAGWILL, Primary Examiner

UNITED STATES PATENT OFFICE
CERTIFICATE OF CORRECTION

Patent No. PP 3,190 Dated May 23, 1972

Inventor(s) HARRY B. WILFONG

It is certified that error appears in the above-identified patent and that said Letters Patent are hereby corrected as shown below:

Column 2, lines 7, 8 and 9, under the heading "White Pink Chief", cancel " 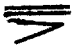 "

Signed and sealed this 22nd day of January 1974.

(SEAL)
Attest:

EDWARD M.FLETCHER,JR.
Attesting Officer

RENE D. TEGTMEYER
Acting Commissioner of Patents